United States Patent
Enerson et al.

(10) Patent No.: US 11,938,278 B2
(45) Date of Patent: Mar. 26, 2024

(54) VASCULAR INTRODUCER SYSTEM WITH INTERLOCKING DEFLECTABLE GUIDING CATHETER SHEATHS

(71) Applicant: Oscor Inc., Palm Harbor, FL (US)

(72) Inventors: Andrew J. Enerson, New Port Richey, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 422 days.

(21) Appl. No.: 17/223,272

(22) Filed: Apr. 6, 2021

(65) Prior Publication Data

US 2021/0308417 A1    Oct. 7, 2021

Related U.S. Application Data

(60) Provisional application No. 63/006,503, filed on Apr. 7, 2020.

(51) Int. Cl.
*A61M 25/00* (2006.01)
*A61M 25/01* (2006.01)

(52) U.S. Cl.
CPC .... *A61M 25/0023* (2013.01); *A61M 25/0136* (2013.01); *A61M 2025/0024* (2013.01)

(58) Field of Classification Search
CPC ...... A61M 2025/0175; A61M 25/0133; A61M 25/0023; A61M 25/0136; A61M 25/0147; A61M 25/01

See application file for complete search history.

(56) References Cited

U.S. PATENT DOCUMENTS

| | | | |
|---|---|---|---|
| 9,233,225 B2 * | 1/2016 | Hebert | A61M 25/0138 |
| 9,498,602 B2 | 11/2016 | Osypka et al. | |
| 9,572,957 B2 | 2/2017 | Osypka et al. | |
| 9,907,570 B2 | 3/2018 | Osypka et al. | |
| 9,913,684 B2 | 3/2018 | Osypka | |
| 2012/0109079 A1 * | 5/2012 | Asleson | A61F 2/2427 606/129 |
| 2014/0309661 A1 * | 10/2014 | Sheps | A61F 2/2427 606/130 |

* cited by examiner

*Primary Examiner* — Phillip A Gray
(74) *Attorney, Agent, or Firm* — Michael F. Scalise

(57) ABSTRACT

A vascular introducer system includes a first vascular introducer having an elongated first deflectable catheter sheath defining a lumen having an interior surface with an inner diameter. A tubular insert having a polygonal cross-section is associated with the interior lumen of the first catheter sheath. The system includes a second vascular introducer having an elongated second deflectable catheter sheath defining an exterior surface with an outer diameter that is less than the inner diameter of the interior surface of the first catheter sheath.

20 Claims, 4 Drawing Sheets

VASCULAR INTRODUCER SYSTEM WITH INTERLOCKING DEFLECTABLE GUIDING CATHETER SHEATHS

CROSS-REFERENCE TO RELATED APPLICATIONS

This application claims priority to and the benefit of U.S. Provisional Patent Application No. 63/006,503 filed Apr. 7, 2020, the entire contents of which is incorporated herein by reference in its entirety.

BACKGROUND OF THE INVENTION

1. Field of the Invention

The subject invention is directed to surgical instrumentation, and more particularly, to a mechanism for interlocking two steerable vascular introducer sheaths together while permitting both to move freely in a longitudinal direction relative to one another.

2. Description of Related Art

The use of steerable guiding sheaths that are deflectable is now standard practice for vascular access and delivery of therapeutic devices such as stents, anchors and drugs to targeted areas in the vascular system of the human body. Deflectable sheaths can be uni-directional or bi-directional, and they are typically available in sheath ID French sizes ranging from 4 F to 20 F. These devices can be designed with deflection angles that vary from 90 degrees to 270 degrees, and they can be designed with various tip formations, shaft stiffness and handle configurations.

Examples of steerable guiding sheaths with deflectable distal end portions that are adapted and configured for use in conjunction with the subject invention are disclosed in commonly assigned U.S. Pat. Nos. 9,498,602; 9,572,957; 9,907,570; and 9,913,684, the disclosures of which are herein incorporated by reference in their entities.

Typically, steerable guiding sheaths feature a PTFE liner that may be reinforced by an embedded braid and/or a coil. These devices typically feature a hemostatic valve at the proximal end of the handle for sealing the interior lumen extending therethrough. The deflection curve of the distal end of the sheath allows a physician to access complex vasculature in a very short period of time, as compared to the use of a non-deflectable sheath that has a fixed distal curvature.

Typically, deflectable sheaths feature a deflection curve whereby the distal tip deflects in a single plane. While deflection in a single plane is often sufficient for vascular access and cardiac access, there are applications where it is beneficial to have two deflectable catheters inserted at the same time: one deflectable outer catheter to access one location, followed by the insertion of a smaller inner catheter to gain access to a second curvature or area.

Since the human body and the vascular system varies from person to person, it is desirable for the inner catheter to be moved freely axially or longitudinally relative to the outer catheter, however once the correct position is found, both catheters should be locked together to inhibit relative rotational or radial motion.

SUMMARY OF THE INVENTION

A vascular introducer system includes a first vascular introducer having an elongated first deflectable catheter sheath defining a lumen having an interior surface with an inner diameter. A tubular insert has a polygonal cross-section and is associated with the interior lumen of the first catheter sheath. The system includes a second vascular introducer having an elongated second deflectable catheter sheath defining an exterior surface with an outer diameter that is less than the inner diameter of the interior surface of the first catheter sheath.

A tubular coupling has a polygonal cross-section that complements the polygonal cross-section of the tubular insert and is associated with the exterior surface of the second catheter sheath, such that when the second catheter sheath is inserted into the lumen of the first catheter sheath, the tubular coupling engages the tubular insert in a manner that permits relative longitudinal motion of the first and second catheter sheaths while inhibiting relative rotational motion of the first and second catheter sheaths, so that the first and second catheter sheaths can be deflected in unison and independently.

The tubular insert and the tubular coupling can be distally located as to their respective catheter sheaths, or can be located at a mid-portion as to their respective catheter sheaths, between the distal end portion and a proximal handle portion. The polygonal cross-section of the tubular insert and the tubular coupling can be octagonal.

The first and second vascular introducers each have a proximal handle assembly that includes a mechanism to effectuate deflection of a distal end portion of the catheter sheath associated therewith. The mechanism includes a rotating control knob such that rotation of the control knob along a longitudinal axis effectuates deflection of a distal end portion of the catheter sheath, where deflection of the first catheter sheath is dominant over deflection of the second catheter sheath. Rotating the control knob of the first vascular introducer effectuates deflection of the distal end portions of both the first and second catheter sheaths in the same direction. Rotating the control knob of the second vascular introducer effectuates deflection of only the distal end portion of the second catheter sheath in the same and/or in a different direction relative to the first catheter sheath.

The mechanism to effectuate deflection of a distal end portion of the first catheter sheath can be the same as the mechanism to effectuate deflection of a distal end portion of the second catheter sheath. The proximal handle portions of the first and second vascular introducers also include a side port tube in fluid communication with the interior lumen of the respective catheter sheath, and the side port tube can be controlled by way of a manual control valve. The second vascular introducer includes an interior lumen extending therethrough for accommodating passage of a surgical device therethrough A method comprises providing a first vascular introducer having an elongated first deflectable catheter sheath defining an interior lumen having an interior surface with an inner diameter and a tubular insert associated with the interior lumen of the first catheter sheath, providing a second vascular introducer having an elongated second deflectable catheter sheath defining an exterior surface with an outer diameter that is less than the inner diameter of the interior surface of the first catheter sheath and an associated tubular insert, inserting the second vascular introducer into the interior lumen of the first deflectable catheter sheath of the first vascular introducer, engaging the tubular coupling associated with the exterior surface of the second catheter sheath with the tubular insert associated with the interior lumen of the first catheter sheath, and actuating a mechanism provided on a proximal handle assembly of at least one of the first and second vascular introducers to effectuate deflection of a distal end portion of a respective one of the first and second vascular introducers.

Engaging the tubular coupling with the tubular insert permits relative longitudinal motion of the first and second catheter sheaths while inhibiting relative rotational motion of the first and second catheter sheaths so that the first and second catheter sheaths can be deflected in unison and independently. Actuating the mechanism of the proximal handle portion of each of the first and second vascular introducers includes rotating a control knob along a longitudinal axis to effectuate deflection of a distal end portion of each of the first and second vascular introducers. Rotating the control knob of the first vascular introducer effectuates deflection of the distal end portions of both the first and second catheter sheaths in the same direction. Rotating the control knob of the second vascular introducer effectuates deflection of only the distal end portion of the second catheter sheath in the same and/or in a different direction than the first catheter sheath, relative to the first catheter sheath.

The method can further include introducing a surgical device through an interior lumen of the second vascular introducer, and introducing a fluid through a side port tube of the proximal handle assembly in fluid communication with the interior lumen of the respective catheter sheath. Introducing fluid flow through the side port tube can be controlled by way of a manual control valve.

These and other features of the vascular introducer system of the subject invention will become more readily apparent to those having ordinary skill in the art to which the subject invention appertains from the following description of the drawings.

BRIEF DESCRIPTION OF THE DRAWINGS

So that those skilled in the art will readily understand how to make and use the vascular introducer system of the subject invention without undue experimentation, reference may be made to the figures wherein.

DETAILED DESCRIPTION OF THE PREFERRED EMBODIMENTS

Figure 1:
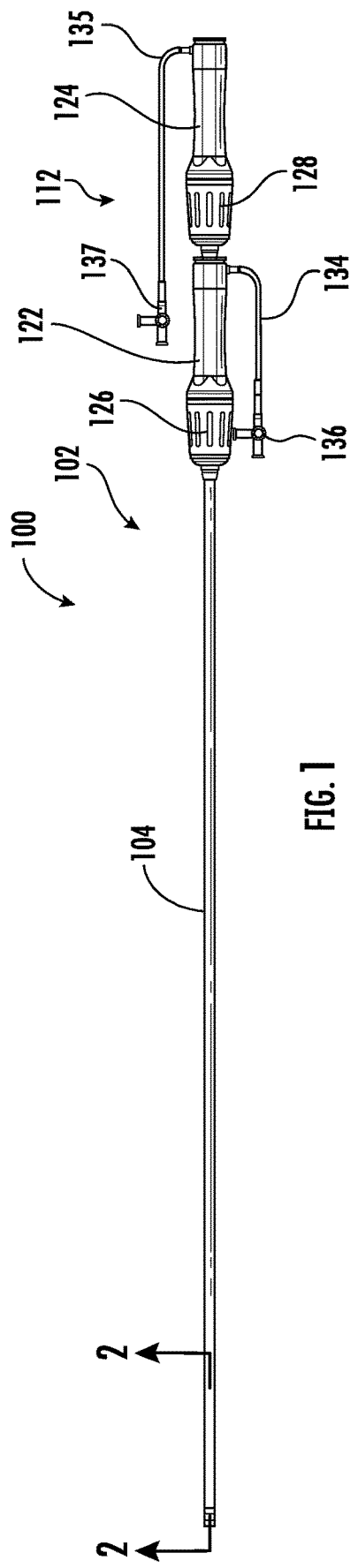
FIG. 1 is a side elevational view of the vascular introducer system of the subject invention, with the second vascular introducer inserted into the first vascular introducer.
Figure 2:
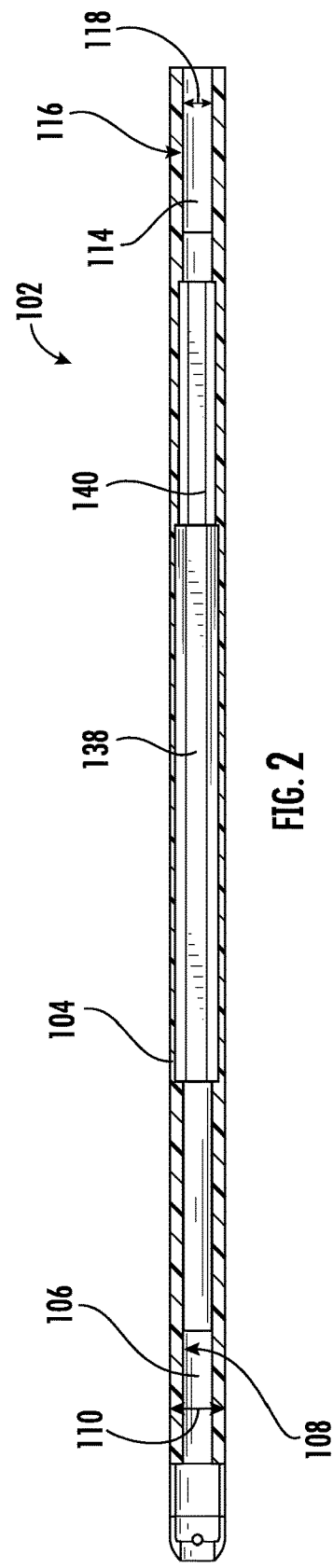
FIG. 2 is a top cross-sectional view of the distal end portion of the system of FIG. 1 to illustrate the engagement of the tubular insert and the tubular coupling.
Figure 3:
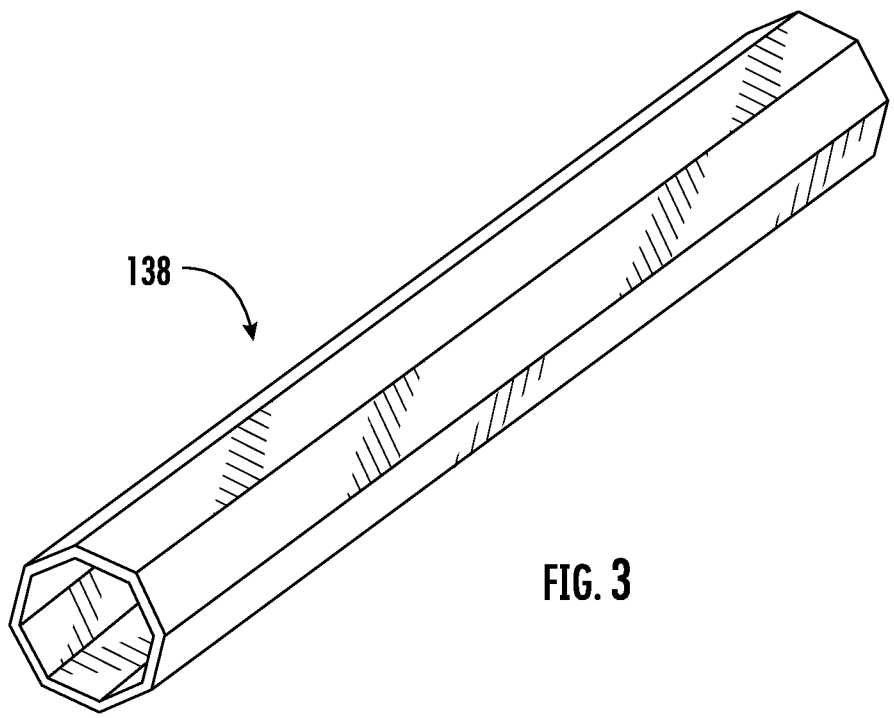
FIG. 3 is an enlarged perspective view of a tubular insert.
Figure 4:
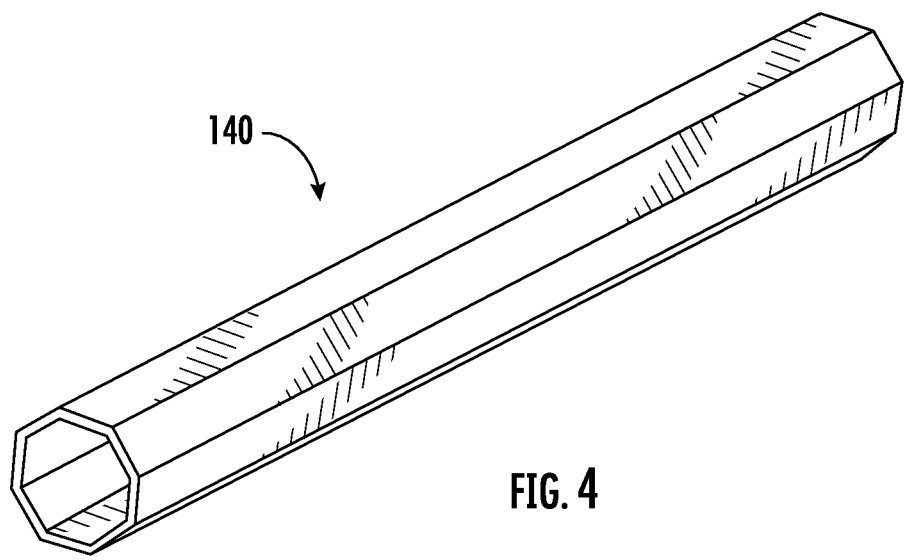
FIG. 4 is an enlarged perspective view of the tubular coupling.
Figure 5:
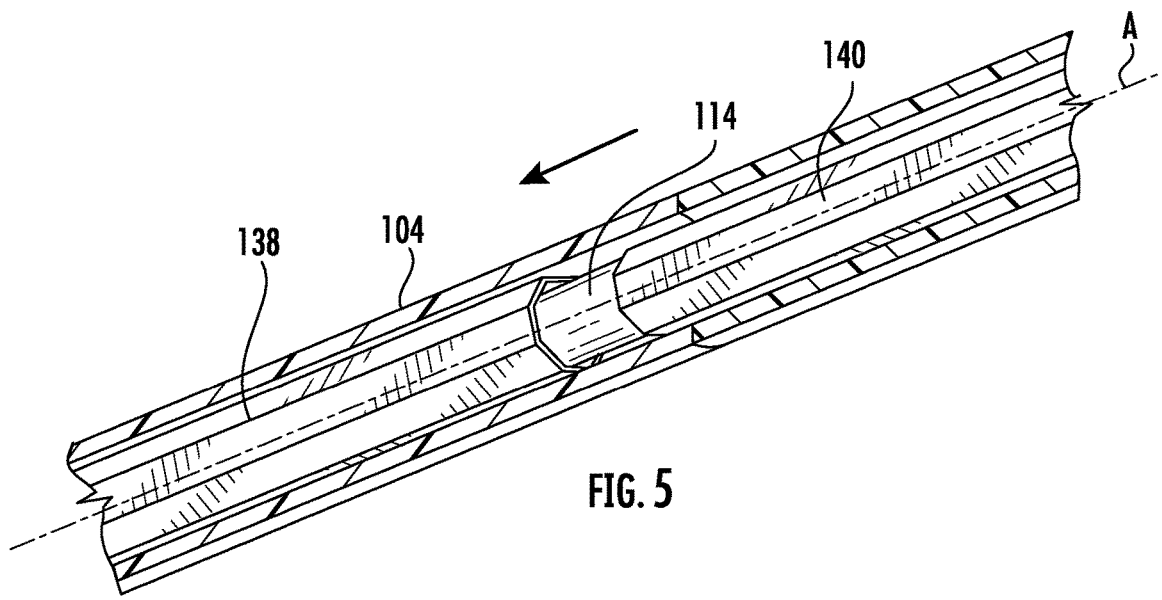
FIGS. 5-6 is a partial side cross-sectional perspective view of the system of FIG. 1 to illustrate the cooperative engagement of the tubular insert and the tubular coupling of FIGS. 3-4.
Figure 6:
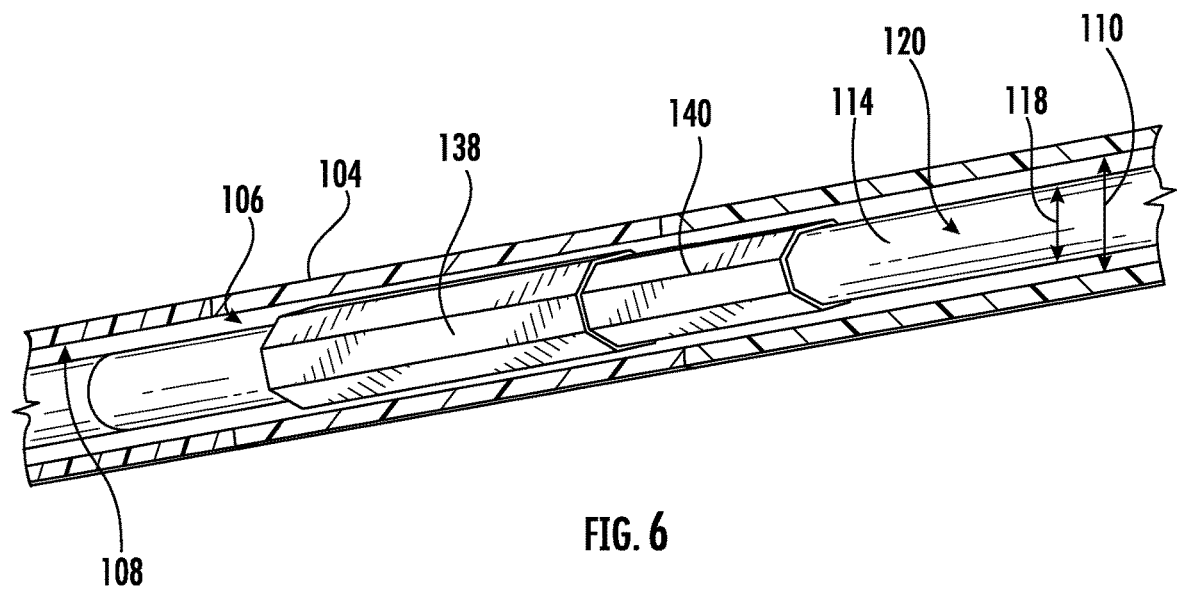

Reference will now be made to the drawings wherein like reference numerals identify similar structural features or aspects of the subject disclosure. For purposes of explanation and illustration, and not limitation, a partial view of an embodiment of a system in accordance with the disclosure is shown in FIG. 1 and is designated generally by reference character 100. Other embodiments of systems in accordance with the disclosure, or aspects thereof, are provided in FIGS. 2-8, as will be described. The systems and methods described herein can be used to increase the curve capability of a vascular introducer.

The present invention is directed to a new and useful vascular introducer system 100 for use in an interventional surgical procedure performed in the vasculature of a patient. The vascular introducer system 100 includes a first vascular introducer 102 having an elongated first deflectable catheter sheath 104 defining a lumen 106, the lumen 106 having an interior surface 108 with an inner diameter 110. A second vascular introducer 112 has an elongated second deflectable catheter sheath 114 that defines an exterior surface 116. An outer diameter 118 of the second deflectable catheter sheath 114 is less than the inner diameter 110 of the interior surface 108 of the first catheter sheath 104 such that the second deflectable catheter sheath 114 is able to be inserted within the first catheter sheath 104. The second vascular introducer 112 additionally includes an interior lumen 120 extending therethrough for accommodating passage of a surgical device (e.g. a stent, anchor, and the like).

The first and second vascular introducers 102,112 each have a proximal handle assembly 122,124. Each handle assembly 122,124 can include a mechanism 126,128 to effectuate deflection of a distal end portion 130,132 of the respective catheter sheath 104,114 associated therewith. For example, the mechanism includes a rotating control knob such that rotation of the control knob 126,128 along longitudinal axis A (FIG. 5) effectuates deflection of the distal end portion 130,132 of the respective catheter sheath 104,114. The proximal handle assemblies 122,124 include a side port tube 134,135 in fluid communication with the interior lumen 106,120 of the respective catheter sheath 104,114. The side port tube 134,135 allows for introduction of fluid into the patient through the respective vascular introducer 102,112 and can be controlled by way of a valve 136,137, such as a manual control valve.

The first deflectable catheter sheath 104 includes a tubular insert 138 having a polygonal (e.g. hexagonal or octagonal) cross-section that is associated with the interior lumen 106 of the first catheter sheath 104. A tubular coupling 140 is associated with the exterior surface 116 of the second catheter sheath 114. In embodiments, the tubular insert 138 and the tubular coupling 140 can be distally located as to their respective catheter sheaths 104,114, or can be centrally located, such as at a mid-portion between the distal end portions 130,132 and the proximal handle assembly 122, 124.

The tubular coupling 140 also has a polygonal cross-section that can be the same or otherwise complement the polygonal cross-section of the tubular insert 138 for engagement with the tubular insert 138. For example, when the second catheter sheath 114 is inserted into the lumen 106 of the first catheter sheath 104, the tubular coupling 140 can engage the tubular insert 138 in a manner that permits relative longitudinal motion (e.g. along axis A) of the first and second catheter sheaths 104,114 while inhibiting relative rotational motion (e.g. about axis A) of the first and second catheter sheaths 104,114. The first and second catheter sheaths 104,116 can thus be deflected in unison and independently.

Figure 7:
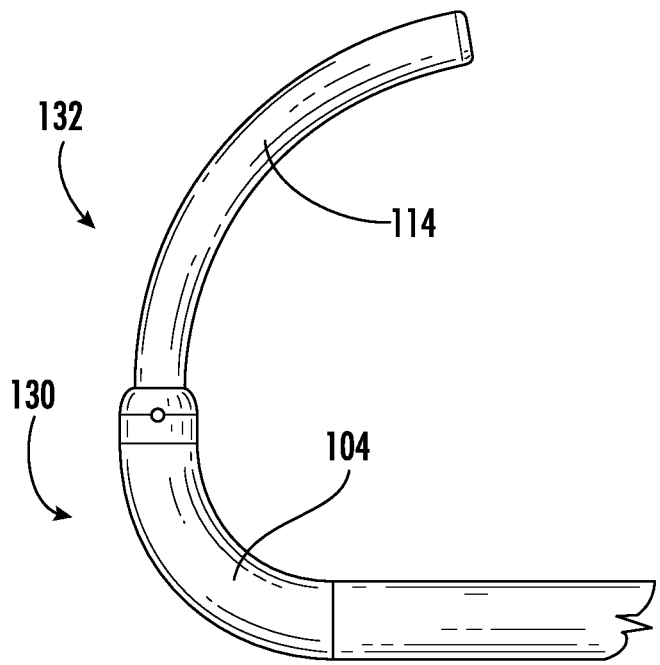
FIG. 7 illustrates the distal end portion of the system of FIG. 1 when the inner sheath is deflected in unison with the outer sheath.
Figure 8:
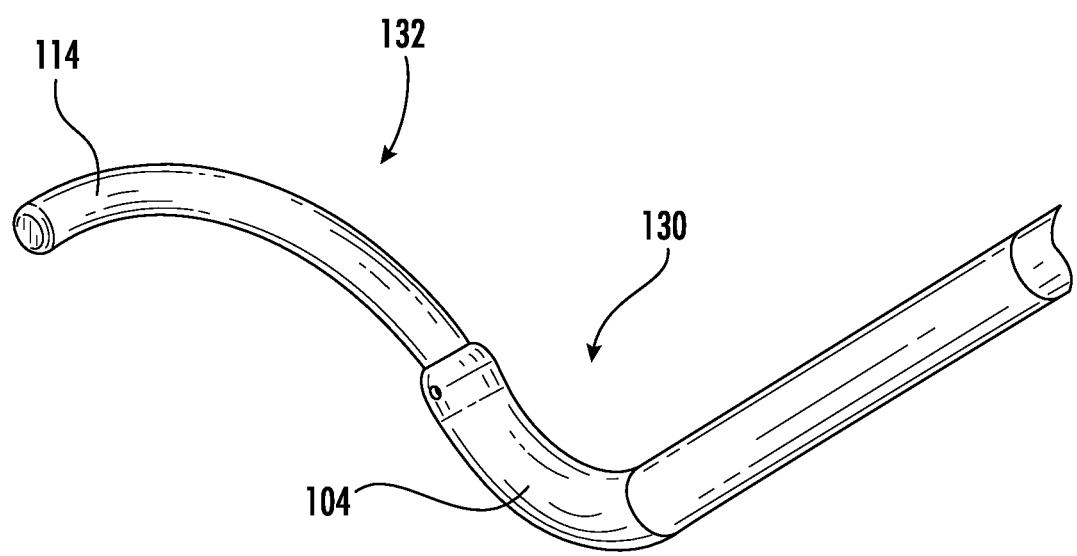
FIG. 8 illustrates the distal end portion of the system of FIG. 1 when the inner sheath is deflected independent from the outer sheath, to achieve a dual curvature.

Deflection of the first catheter sheath 104 is dominant over the deflection of the second catheter sheath 114. In this manner, as shown in FIG. 7, rotating the first control knob 126 will result in unison, unidirectional deflection of the distal end portions 130,132, achieving additional turn radius as compared to a traditional vascular introducer. As shown in FIG. 8, rotating the second control knob 128 will result in independent, bi-directional deflection of the distal end portions 130,132, allowing the system 100 to navigate through a tortuous vasculature. More specifically, rotating the first control knob 126 will effectuate deflection of the distal end portions 130,132 of both the first and second catheter sheaths 104,114, while rotating the second control knob 128 will effectuate deflection of only the distal end portion 132 of the second catheter sheath 114, whether in the same, or in a different direction than the already deflected first catheter sheath 104, relative to the first catheter sheath 104. Any other suitable mechanism for effectuating deflection is contemplated herein, for example a pivoting handle portion.

Further, deflection of the second catheter sheath 114 is dependent on the interaction with the first catheter sheath 104 (e.g., the relative angular orientation about the common axis A), therefore, repositioning the second catheter sheath 114 before engaging the tubular coupling 140 with the tubular insert 138 will produce varied deflective responses. For example, rotating the second catheter sheath 114 any number of degrees out of phase as allowed for by the polygonal shape of the tubular insert 138 and tubular coupling 140 will produce a respective number of differing deflection orientations (e.g., six for a hexagonal shape, eight for an octagonal shape) between the first catheter sheath 104 and the second catheter sheath 114.

A method for vascular introduction includes providing the first vascular introducer 102, providing the second vascular introducer 112, and inserting the second vascular introducer 112 into the first vascular introducer 102, for example through the lumen 106 of the first deflectable catheter sheath 104. The method includes engaging the tubular coupling 140 associated with the exterior surface 116 of the second catheter sheath 114 with the tubular insert 138 associated with the interior lumen 106, and actuating the mechanism (e.g. control knobs 126,128) provided on the proximal handle assembly 122,124 of each of the first and second vascular introducers 102,112 to effectuate deflection of a distal end portion 130,132 of the respective one of the first and second vascular introducers 102,112.

The method further includes introducing a surgical device (e.g. a stent, anchor) through the interior lumen 120 of the second vascular introducer 112, and introducing a fluid through a side port tube 134,135 of the proximal handle assembly 122,124, where fluid flow through the side port is controllable by way of the manual valve 136,137 provided on the side port tube 134,135.

The methods and systems of the present disclosure, as described above and shown in the drawings, provide for improved reach and curve capability of a distal end portion of the vascular introducer. While the apparatus and methods of the subject disclosure have been shown and described, those skilled in the art will readily appreciate that changes and/or modifications may be made thereto without departing from the scope of the subject disclosure.

What is claimed is:

1. A vascular introducer system, comprising:
   a) a first vascular introducer comprising a deflectable first catheter sheath extending along a first longitudinal axis to a first distal end portion, the first catheter sheath defining a first lumen having a first interior surface with a first inner diameter, wherein a first tubular insert having either a first hexagonally-shaped or a first octagonally-shaped cross-section perpendicular to the first longitudinal axis is connected to the first interior surface of the first catheter sheath; and
   b) a second vascular introducer comprising a deflectable second catheter sheath extending along a second longitudinal axis to a second distal end portion, the second catheter sheath defining a second exterior surface with a second outer diameter that is less than the first inner diameter of the first interior surface of the first catheter sheath, wherein a second tubular coupling having either a second hexagonally-shaped or a second octagonally-shaped cross-section perpendicular to the second longitudinal axis and that is the same shape as the first tubular insert is connected to the second exterior surface of the second catheter sheath,
   c) wherein, when the second catheter sheath is inserted into the first lumen of the first catheter sheath so that the first and second longitudinal axes are co-axially aligned, the second hexagonally-shaped or the second octagonally-shaped tubular coupling engages the corresponding first hexagonally-shaped or the first octagonally-shaped tubular insert of the first catheter sheath to provide for relative longitudinal movement while inhibiting relative rotational movement of the first and second catheter sheaths so that the first and second distal end portions can be deflected in unison and independently.

2. The vascular introducer system of claim 1, wherein the first vascular introducer has a first handle assembly connected to the first catheter sheath, the first handle assembly comprising a first mechanism, and wherein the second vascular introducer has a second handle assembly connected to the second catheter sheath, the second handle assembly comprising a second mechanism, and wherein the first and second mechanisms are configured to effectuate deflection of the respective first and second distal end portions of the first and second catheter sheaths.

3. The vascular introducer system of claim 2, wherein the first mechanism is a first rotatable control knob that is configured to effectuate deflection of the first distal end portion of the first catheter sheath, and the second mechanism is a second rotatable control knob that is configured to effectuate deflection of the second distal end portion of the second catheter sheath, and wherein independent rotation of the first and second control knobs about the co-axially aligned first and second longitudinal axes effects independent deflection of the respective first and second distal end portions of the first and second catheter sheaths.

4. The vascular introducer system of claim 2, wherein the first and second mechanisms are the same type of mechanism.

5. The vascular introducer system of claim 1, wherein deflection of the first distal end portion is dominant over deflection of the second distal end portion so that deflection of the first distal end portion of the first catheter sheath causes deflection of the second distal end portion of the second catheter sheath.

6. The vascular introducer system of claim 3, wherein rotation of the first control knob effects deflection of the first and second distal end portions of the respective first and second catheter sheaths in the same direction.

7. The vascular introducer system of claim 3, wherein, relative to the first catheter sheath, rotation of the second control knob effectuates deflection of only the second distal end portion of the second catheter sheath in the same or a different direction with respect to the first distal end portion of the first catheter sheath.

8. The vascular introducer system of claim 2, wherein the second catheter sheath defines a second lumen, and wherein at least one of the first and second proximal handle assemblies of the respective first and second vascular introducers comprises a side port tube in fluid communication with the corresponding first and second lumen of the respective first and second catheter sheaths.

9. The vascular introducer system of claim 8, wherein the side port tube includes a manual valve.

10. The vascular introducer system of claim 1, wherein the second catheter sheath comprises a second lumen that is configured for passage of a surgical device therethrough.

11. The vascular introducer system of claim 1, wherein the first tubular insert of the first catheter sheath and the second tubular coupling of the second catheter sheath are proximally located relative to their respective first and second distal end portions.

12. The vascular introducer system of claim 1, wherein the first tubular insert of the first catheter sheath and the second tubular coupling of the second catheter sheath are located at about a mid-portion between the first and second handle assemblies and the first and second distal end portions of the respective first and second catheter sheaths.

13. A method, comprising:
   a) providing a first vascular introducer comprising a deflectable first catheter sheath extending along a first longitudinal axis to a first distal end portion, the first handle assembly comprising a first mechanism that is configured to effectuate deflection of the first distal end portion of the first catheter sheath, wherein the first catheter sheath comprises a first interior surface defining a first lumen having a first inner diameter, and connecting a first tubular insert comprising either a first hexagonally-shaped or a first octagonally-shaped cross-section perpendicular to the first longitudinal axis to the first interior surface of the first catheter sheath;
   b) providing a second vascular introducer comprising a second handle assembly connected to a deflectable second catheter sheath extending along a second longitudinal axis to a second distal end portion, the second handle assembly comprising a second mechanism that is configured to effectuate deflection of the second distal end portion of the second catheter sheath, wherein the second catheter sheath comprises a second exterior surface defining a second outer diameter that is less than the first inner diameter of the first interior surface of the first catheter sheath, and connecting a second tubular coupling comprising either a second hexagonally-shaped or a second octagonally-shaped cross-section perpendicular to the second longitudinal axis to the exterior surface of the second catheter sheath, wherein the first tubular insert and the second tubular coupling have the same hexagonal or octagonal shape;
   c) inserting the second catheter sheath of the second vascular introducer into the interior lumen of the first catheter sheath of the first vascular introducer;
   d) engaging the second tubular coupling connected to the exterior surface of the second catheter sheath with the first tubular insert connected to the first interior surface of the first catheter sheath; and
   e) actuating at least one of the first and second mechanisms of the respective first and second handle assemblies to effectuate deflection of at least one of the first and second distal end portions of the respective first and second vascular introducers.

14. The method of claim 13, wherein engaging the second tubular coupling with the first tubular insert provides for relative longitudinal movement while inhibiting relative rotational movement of the first and second catheter sheaths so that the first and second catheter sheaths can be deflected in unison and independently.

15. The method of claim 13, wherein the first mechanism is a first rotatable control knob that is configured to effectuate deflection of the first distal end portion of the first catheter sheath, and the second mechanism is a second rotatable control knob that is configured to effectuate deflection of the second distal end portion of the second catheter sheath, the method further including independently rotating the first and second control knobs about the co-axially aligned first and second longitudinal axes to effect independent deflection of the respective first and second distal end portions of the first and second catheter sheaths.

16. The method of claim 15, wherein rotating the first control knob of the first vascular introducer effectuates deflection of the first and second distal end portions of the respective first and second catheter sheaths in the same direction, and wherein rotating the second control knob of the second vascular introducer effectuates deflection of only the second distal end portion of the second catheter sheath in the same or a different direction with respect to the first distal end portion of the first catheter sheath.

17. The method of claim 13, wherein the second catheter sheath comprises a second lumen, and further comprising introducing a surgical device through the second lumen of the second vascular introducer.

18. The method of claim 13, wherein the second catheter sheath defines a second lumen, and wherein at least one of the first and second proximal handle assemblies of the respective first and second vascular introducers comprises a side port tube in fluid communication with the corresponding first and second lumen of the respective first and second catheter sheaths, further comprising introducing a fluid through the side port tube of the at least one of the first and second proximal handle assemblies in fluid communication with the corresponding first and second lumen of the respective first and second catheter sheaths.

19. The method of claim 18, further comprising controlling fluid flow through the side port tube using a manual control valve.

20. The method of claim 13, including positioning the first tubular insert of the first catheter sheath and the second tubular coupling of the second catheter sheath at about a mid-portion between the first and second handle assemblies and the first and second distal end portions of the respective first and second catheter sheaths.

* * * * *